(12) United States Patent
Cohen et al.

(10) Patent No.: US 8,273,105 B2
(45) Date of Patent: Sep. 25, 2012

(54) COMPOUND BARB MEDICAL DEVICE AND METHOD

(75) Inventors: Matthew D. Cohen, Berlin, CT (US);
Nicholas Maiorino, Branford, CT (US);
Timothy D. Kosa, Hamden, CT (US);
Mark S. Buchter, Ansona, CT (US);
Michael Primavera, Orange, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 380 days.

(21) Appl. No.: 12/361,962

(22) Filed: Jan. 29, 2009

(65) Prior Publication Data
US 2009/0210006 A1   Aug. 20, 2009

Related U.S. Application Data

(60) Provisional application No. 61/029,964, filed on Feb. 20, 2008.

(51) Int. Cl.
*A61B 17/04* (2006.01)
(52) U.S. Cl. ..................................................... 606/228
(58) Field of Classification Search ........... 606/228–231
See application file for complete search history.

(56) References Cited

U.S. PATENT DOCUMENTS

| | | |
|---|---|---|
| 3,123,077 A | 3/1964 | Alcamo |
| 3,657,056 A | 4/1972 | Winston et al. |
| 4,024,871 A | 5/1977 | Stephenson |
| 5,019,093 A | 5/1991 | Kaplan et al. |
| 5,059,213 A | 10/1991 | Chesterfield et al. |
| 5,123,913 A | 6/1992 | Wilk et al. |
| 5,133,738 A | 7/1992 | Korthoff et al. |
| 5,181,923 A | 1/1993 | Chesterfield et al. |
| 5,226,912 A | 7/1993 | Kaplan et al. |
| 5,236,563 A | 8/1993 | Loh |
| 5,261,886 A | 11/1993 | Chesterfield et al. |
| 5,306,289 A | 4/1994 | Kaplan et al. |
| 5,318,575 A | 6/1994 | Chesterfield et al. |
| 5,342,376 A | 8/1994 | Ruff |
| 5,370,031 A | 12/1994 | Koyfman et al. |
| 5,383,387 A | 1/1995 | Chesterfield et al. |
| 5,383,883 A | 1/1995 | Wilk et al. |
| 5,417,700 A | 5/1995 | Egan |
| 5,569,302 A | 10/1996 | Proto et al. |

(Continued)

FOREIGN PATENT DOCUMENTS

EP   0 326 426 A2   8/1989

(Continued)

OTHER PUBLICATIONS

European Search Report for EP 10177651.6-1526 date of completion is Dec. 14, 2010 (3 pages).

(Continued)

*Primary Examiner* — Corrine M McDermott
*Assistant Examiner* — Gregory Anderson

(57) ABSTRACT

A compound barb medical device is provided which includes an elongated body having at least one barb formed along the length of the body, the barb defining an inner surface with a first portion disposed at a first orientation relative to a longitudinal axis of the elongated body, and a second portion disposed at a second orientation relative to the longitudinal axis. Optionally, the barb defines a third portion disposed at a third orientation relative to the longitudinal axis. A method for forming a compound barb on a medical device is also provided.

9 Claims, 12 Drawing Sheets

U.S. PATENT DOCUMENTS

| | | | |
|---|---|---|---|
| 5,662,682 | A | 9/1997 | Chesterfield et al. |
| 5,667,528 | A | 9/1997 | Colligan |
| 5,683,417 | A | 11/1997 | Cooper |
| 5,814,056 | A | 9/1998 | Prosst et al. |
| 5,893,880 | A | 4/1999 | Egan et al. |
| 5,931,855 | A | 8/1999 | Buncke |
| 5,964,765 | A | 10/1999 | Fenton, Jr. et al. |
| 6,063,105 | A | 5/2000 | Totakura |
| 6,106,505 | A | 8/2000 | Modak et al. |
| 6,143,352 | A | 11/2000 | Clark et al. |
| 6,165,202 | A | 12/2000 | Kokish et al. |
| 6,174,324 | B1 | 1/2001 | Egan et al. |
| 6,203,564 | B1 | 3/2001 | Hutton et al. |
| 6,217,591 | B1 | 4/2001 | Egan et al. |
| 6,235,869 | B1 | 5/2001 | Roby et al. |
| 6,241,747 | B1 | 6/2001 | Ruff |
| 6,286,746 | B1 | 9/2001 | Egan et al. |
| 6,488,690 | B1 | 12/2002 | Morris et al. |
| 6,506,197 | B1 | 1/2003 | Rollero et al. |
| 6,562,051 | B1 | 5/2003 | Bolduc et al. |
| 6,599,310 | B2 | 7/2003 | Leung et al. |
| 6,620,846 | B1 | 9/2003 | Jonn et al. |
| 6,692,499 | B2 | 2/2004 | Tormala et al. |
| 6,773,450 | B2 | 8/2004 | Leung et al. |
| 6,923,824 | B2 | 8/2005 | Morgan et al. |
| 7,090,111 | B2 | 8/2006 | Egan et al. |
| 2002/0077661 | A1 | 6/2002 | Saadat |
| 2002/0177876 | A1 | 11/2002 | Roby et al. |
| 2003/0074023 | A1 | 4/2003 | Kaplan et al. |
| 2003/0097148 | A1 | 5/2003 | Valimaa et al. |
| 2003/0149447 | A1 | 8/2003 | Morency et al. |
| 2004/0010275 | A1 | 1/2004 | Jacobs et al. |
| 2004/0030354 | A1 | 2/2004 | Leung et al. |
| 2004/0060409 | A1 | 4/2004 | Leung et al. |
| 2004/0060410 | A1 | 4/2004 | Leung et al. |
| 2004/0087974 | A1 | 5/2004 | Bittar |
| 2004/0088003 | A1 | 5/2004 | Leung et al. |
| 2004/0122451 | A1 | 6/2004 | Wood |
| 2004/0153125 | A1 | 8/2004 | Roby |
| 2004/0162580 | A1 | 8/2004 | Hain |
| 2005/0033367 | A1 | 2/2005 | Leung et al. |
| 2005/0165448 | A1 | 7/2005 | Egan et al. |
| 2005/0209639 | A1 | 9/2005 | Gidwani et al. |
| 2005/0216058 | A1 | 9/2005 | Egan et al. |
| 2005/0267479 | A1 | 12/2005 | Morgan et al. |
| 2005/0267531 | A1 | 12/2005 | Ruff et al. |
| 2006/0111734 | A1 | 5/2006 | Kaplan et al. |
| 2006/0116718 | A1 | 6/2006 | Leiboff |
| 2006/0135995 | A1 | 6/2006 | Rugg et al. |
| 2006/0206096 | A1 | 9/2006 | Accisano, III et al. |
| 2007/0005110 | A1 | 1/2007 | Collier et al. |
| 2007/0021780 | A1 | 1/2007 | Harrington et al. |
| 2007/0187861 | A1 | 8/2007 | Genova et al. |
| 2008/0312688 | A1* | 12/2008 | Nawrocki et al. ............. 606/228 |

FOREIGN PATENT DOCUMENTS

| | | |
|---|---|---|
| EP | 0 499 048 A1 | 8/1992 |
| EP | 0 632 999 A | 1/1995 |
| EP | 0 647 452 A1 | 4/1995 |
| EP | 1 669 093 | 6/2006 |
| EP | 1 656 890 B1 | 12/2008 |
| EP | 2108319 A1 | 10/2009 |
| EP | 2133028 A2 | 12/2009 |
| WO | WO 97/08238 | 3/1997 |
| WO | WO 98/00065 | 1/1998 |
| WO | WO 98/52473 | 11/1998 |
| WO | WO 99/52451 A | 10/1999 |
| WO | WO 00/57933 A1 | 10/2000 |
| WO | WO 01/52751 A | 7/2001 |
| WO | WO 03/001979 A2 | 1/2003 |
| WO | WO 03/088818 A2 | 10/2003 |
| WO | WO 03/088846 A1 | 10/2003 |
| WO | WO 2004/014236 A1 | 2/2004 |
| WO | WO 2004/030520 A2 | 4/2004 |
| WO | WO 2004/030704 A2 | 4/2004 |
| WO | WO 2004/030705 A2 | 4/2004 |
| WO | WO 2004/045663 | 6/2004 |
| WO | WO 2004/066927 | 8/2004 |
| WO | WO 2005/080495 | 1/2005 |
| WO | WO 2006/079469 | 8/2006 |
| WO | WO 2007/133103 A | 11/2007 |
| WO | 2008/045376 A2 | 4/2008 |
| WO | WO 2008/042909 A | 4/2008 |
| WO | WO 2008/107919 A | 9/2008 |
| WO | WO 2008/117328 | 10/2008 |
| WO | WO 2008/141034 A1 | 11/2008 |

OTHER PUBLICATIONS

U.S. Appl. No. 60/994,173, filed Sep. 17, 2007, Maiorino et al.

JLT1204-211-229 (175): R.R. Szarmach et al., Journal of Long-Term Effects of Medical Implants, "An Innovative Surgical Suture and Needle . . . " 12(4), pp. 211-229 (2002).

George Odian, "Principles of Polymerization," III Edition, pp. 569-573 (1991).

International Search Report from Appln. No. EP 06 012688 dated Aug. 1, 2007.

European Search Report from Appln. No. EP 07 253438 dated Feb. 1, 2008.

European Search Report from application No. 07 25 4703 dated Feb. 10, 2009.

European Search Report from application No. 07 25 4341 dated Apr. 20, 2009.

European Search Report for Appln. No. 09251035.3 dated Jun. 3, 2009.

European Search Report for Appln. No. 09250460 dated Jun. 2, 2009.

European Search Report for EP 09250460.4-2310 date of completion is Jun. 2, 2009 (3 pages).

European Search Report for EP 10 25 0848 dated Aug. 12, 2010 (completed Jul. 26, 2010) (3 pages).

European Search Report for European Application No. 10250002.2 dated Mar. 24, 2010. (9 pages).

European Search Report for Application No. EP 08 25 3618 dated Jul. 25, 2011.

European Search Report for EP 12151535.7-2310 date of completion is Mar. 27, 2012 (6 pages).

European Search Report for EP 12151526.6-2310 date of completion is Mar. 23, 2012 (6 pages).

European Search Report for EP 12151532.4-2310 date of completion is Mar. 27, 2012 (6 pages).

European Search Report for EP 12151531.6-2310 date of completion is Mar. 27, 2012 (6 pages).

European Search Report for EP 12151525.8-2310 date of completion is Mar. 27, 2012 (5 pages).

European Search Report for EP 12151530.8-2310 date of completion is Mar. 16, 2012 (6 pages).

European Search Report for EP 12151537.3-2310 date of completion is Mar. 19, 2012 (6 pages).

* cited by examiner

COMPOUND BARB MEDICAL DEVICE AND METHOD

CROSS-REFERENCE TO RELATED APPLICATIONS

This application claims the benefit of and priority to U.S. Provisional Patent Application No. 61/029,964, filed Feb. 20, 2008, the entire disclosure of which is incorporated by reference herein.

TECHNICAL FIELD

The present disclosure relates generally to forming barbs on medical devices. In particular, the present disclosure relates to compound barb medical device and method of forming compound barbs on sutures.

BACKGROUND OF RELATED ART

Barbed sutures are known for use in medical procedures. The configuration of barbs on a barbed suture may be designed to optimize tissue holding for a particular indication. In some circumstances, a random configuration of barbs on the exterior surface of the suture may be preferred to achieve optimal wound closure. However, in other circumstances, where the wound or tissue repair needed is relatively small, a reduced number of barbs may be desired. In still other circumstances, a bidirectional barbed suture may be desirable to permit passing of the suture through tissue in one direction over a portion of the suture and permit passing of the suture through tissue in a second direction over another portion of the suture.

While various methods of forming barbs on sutures have been proposed, such methods may be difficult or costly to implement. Thus, there remains room for improvement with respect to barbed sutures and methods for making them.

SUMMARY

A compound barb medical device is provided which includes an elongated body having at least one barb extending from the elongated body. The barb defines an inner surface, the inner surface includes a first portion disposed at a first orientation relative to a longitudinal axis of the elongated body, a second portion disposed at a second orientation relative to the longitudinal axis, and a third portion disposed at a third orientation relative to the longitudinal axis.

In some embodiments, at least one of the first, second, or third portions of the compound barb is substantially linear. In other embodiments, at least one of the first, second, or third portions of the compound barb is substantially non-linear. In certain embodiments, compound barb medical device is a suture.

In one embodiment, the medical device includes an elongate body wherein the elongate body is a monofilament suture including an outer surface, and the outer surface is in direct contact with tissue, at least one barb extending from the elongated body and defining an inner surface, the inner surface including a first portion disposed at a first orientation relative to a longitudinal axis of the elongate body, wherein the first portion is disposed at a first angle from about 0 degrees to about 90 degrees relative to the longitudinal axis of the elongate body; and a second portion disposed at a second orientation relative to the longitudinal axis of the elongate body, wherein the second portion is disposed at a second angle from about 0 degree to about 90 degrees relative to the longitudinal axis of the elongate body.

A method of forming a compound barb on a medical device in accordance with the present disclosure is provided and includes providing a medical device having a longitudinal axis, applying vibrational energy to a cutting element to form a compound barb on at least a portion of the medical device including forming a first cut in the medical device, the first cut having a first ratio of cut depth to diameter of the medical device; forming a second cut in the medical device, the second cut having a second ratio of cut depth to diameter of the medical device; and optionally forming a third cut in the medical device, the third cut having a third ratio of cut depth to diameter of the medical device. A compound barb medical device formed by said method is also provided.

BRIEF DESCRIPTION OF THE DRAWINGS

Various embodiments of the present disclosure will be described herein below with reference to the figures wherein.

DETAILED DESCRIPTION

Figure 1:
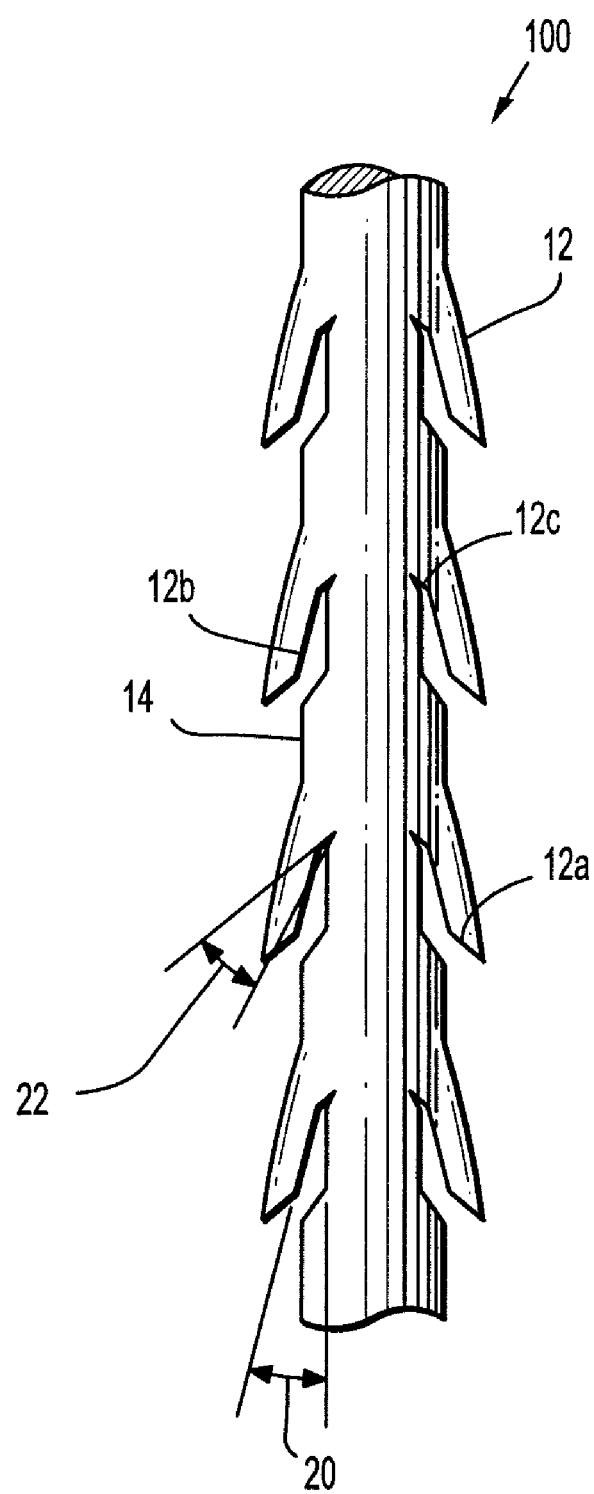
FIG. 1 is a plan view of a barbed suture having compound barbs formed in accordance with the present disclosure.

Referring in detail to the drawings in which like reference numerals are applied to like elements in the various views, FIG. 1 illustrates a medical device 100 having an elongated body 14 and at least one compound barb 12 extending from the elongated body 14. Compound barb 12 defines an inner surface which includes a first portion 12a disposed at a first orientation relative to the longitudinal axis of elongated body 14, a second portion 12b disposed at a second orientation relative to the longitudinal axis, and a third portion 12c disposed at a third orientation relative to the longitudinal axis.

Compound barbs 12 include at least one substantially linear portion. As illustrated in FIG. 1, first, second and third portions 12a-c are substantially linear. It is envisioned that at least one of the portions may be substantially non-linear, such as for example, arcuate as described hereinbelow.

Figure 2:
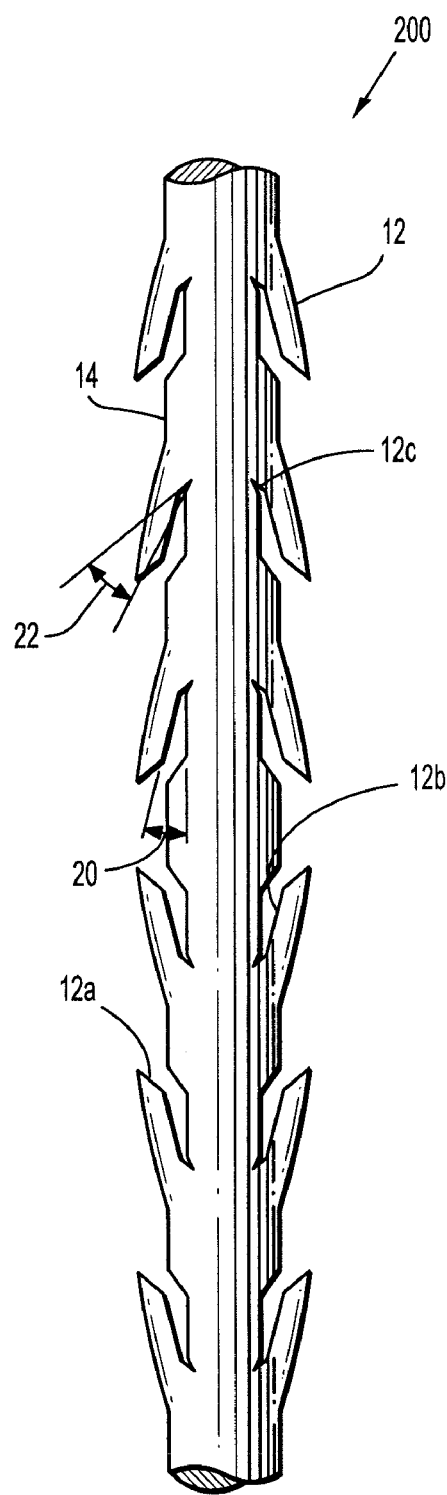
FIG. 2 is a plan view of a two way barbed suture having compound barbs formed in accordance with the present disclosure.

As shown in the exemplary embodiment of FIG. 1, compound barbs 12 may be formed projecting from the medical device 100 towards at least one end. In other alternative embodiments, multiple compound barbs may be formed such that some of the barbs project toward one end and the remaining barbs project toward the other end so as to form a bi-directional medical device 200 as generally illustrated in FIG. 2. Alternatively, a plurality of axially spaced barbs may be formed in the same or random configuration and at different angles in relation to each other. Optionally, the medical device may include a plurality of barbs spaced at the same or different lengths according to the type of tissue being manipulated and/or procedure performed (not shown). In some embodiments, the compound barb medical device incorporates a loop at the proximal end thereof configured to enhance retention of the device in body tissue at a desired position.

Figure 3:
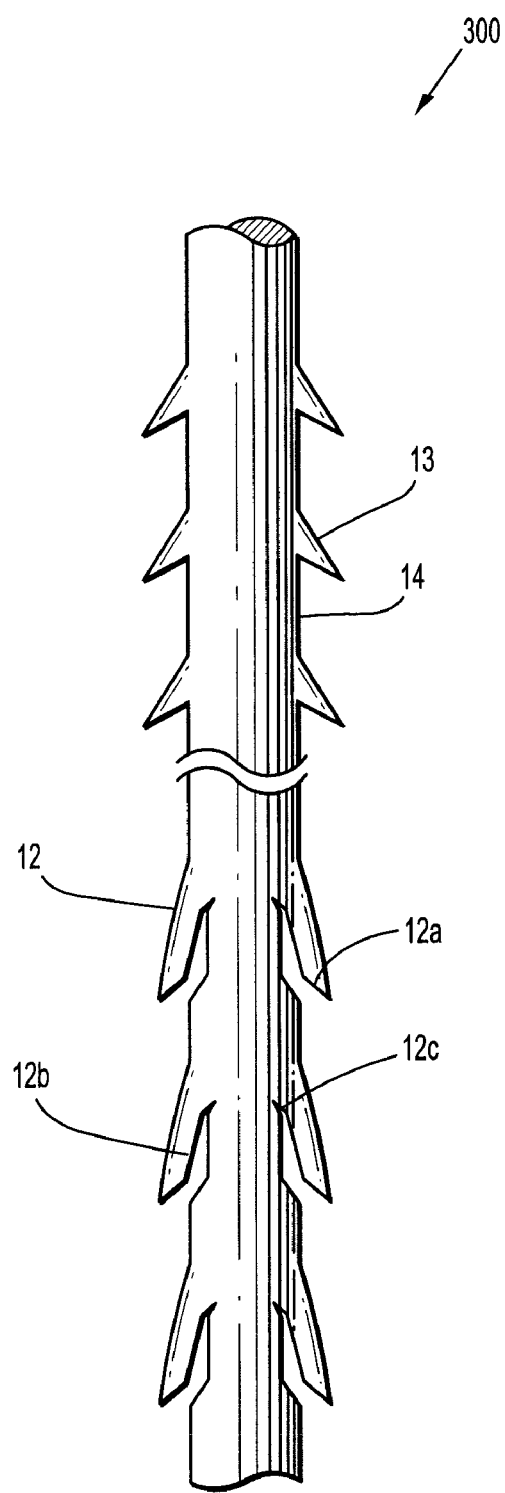
FIG. 3 is a plan view of an alternative embodiment of a barbed suture having both single angle barbs and compound barbs formed in accordance with the present disclosure.

In an alternative embodiment, medical device 300 may be formed to include a combination of compound barbs 12 and single angle barbs 13 as shown in FIG. 3. In such an embodiment, the compound barbs 12 and single angle barbs 13 may be formed along the length of the medical device 300 in specified or random patterns. Additionally, the medical device 300 may be formed such that compound barbs 12 are all oriented in the same direction toward one end of medical device 300 and the single angle barbs 13 are all oriented in the same direction toward the other end of medical device 300.

Figure 4A:
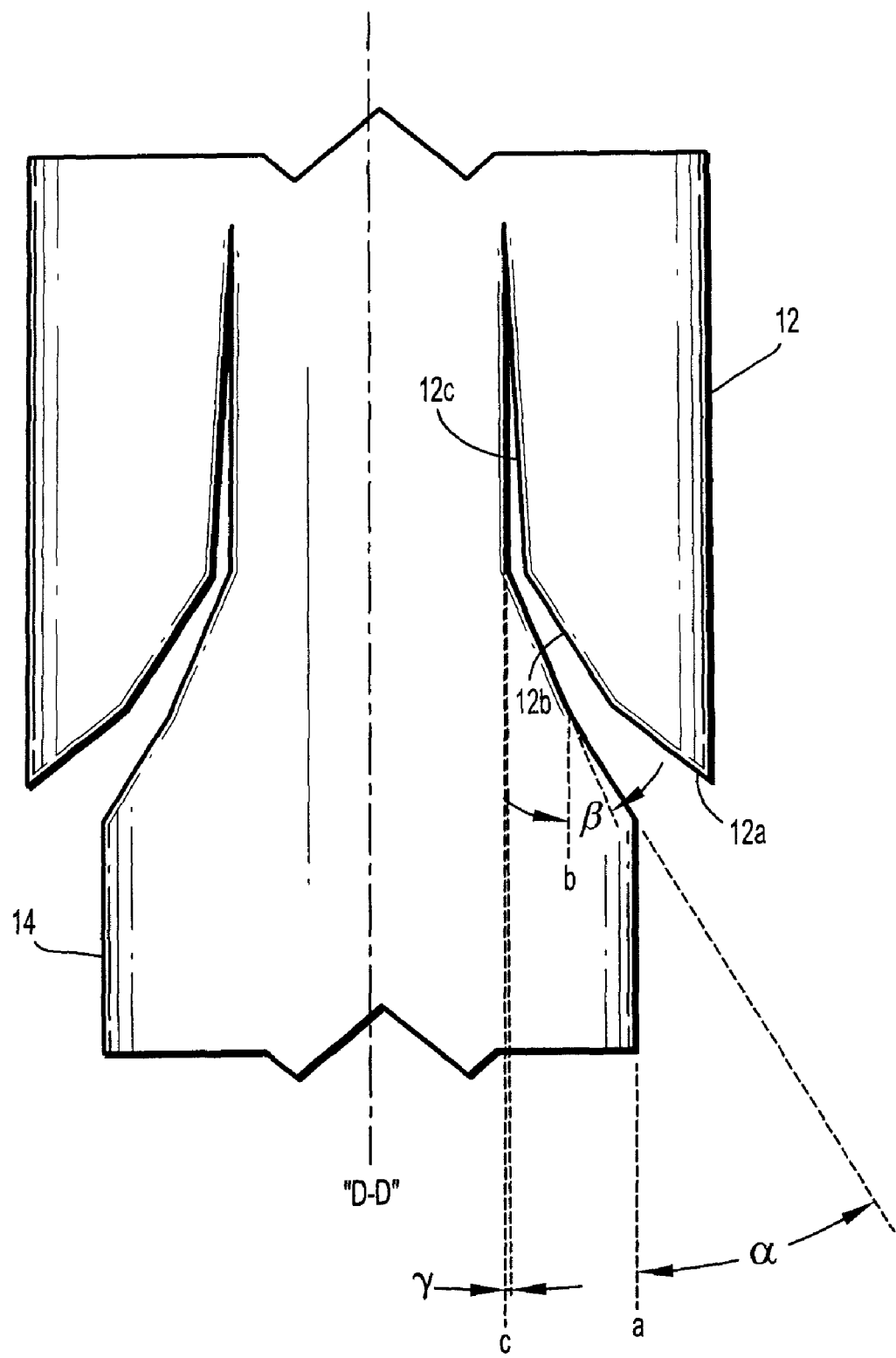
FIG. 4A is a plan view of a segment of a barbed suture having compound barbs formed in accordance with the present disclosure.

Referring to FIG. 4A, compound barbs 12 having first, second and third portions 12a-c are generally formed by cutting into the surface of elongated body 14. In embodiments, each of the first, second, and third portions 12a-c may be cut at first, second and third angles $\alpha$, $\beta$, and $\gamma$ relative to longitudinal axes a, b, and c respectively of elongated body 14 which are parallel to a central longitudinal axis 'D', wherein the second angle $\beta$ is less than the first angle $\alpha$, and the third angle $\gamma$ is less than the second angle $\beta$. Compound barb 12 may include a first portion 12a which is formed by cutting into elongated body 14 at a first angle $\alpha$ of from about 0 degrees to about 90 degrees relative to longitudinal axis "a", in other embodiments, the first angle $\alpha$ ranges from about 30 degrees to about 50 degrees relative to longitudinal axis "a", a second portion 12b which is formed by cutting into elongated body 14 at a second angle $\beta$ of from about 0 degrees to about 90 degrees relative to the longitudinal axis "b", in other embodiments, the second angle $\beta$ ranges from about 2 degrees to about 25 degrees relative to the longitudinal axis "b", and a third portion 12c which is formed by cutting into elongated body 14 at a third angle $\gamma$ of from about 0 degrees to about 90 degrees relative to longitudinal axis "c", in other embodiments, the third angle $\gamma$ ranges from about 2 degrees to about 50 degrees relative to longitudinal axis "c".

In other embodiments, a compound barb medical device includes an elongated body which includes first and second portions, the first and second portions of the elongated body are at first and second angles respective to a longitudinal axis of the elongated body to form at least one compound barb (not shown). Optionally, the elongated body of the compound barb medical device may include a third portion at a third angle respective to a longitudinal axis of the elongated body.

Figure 4B:
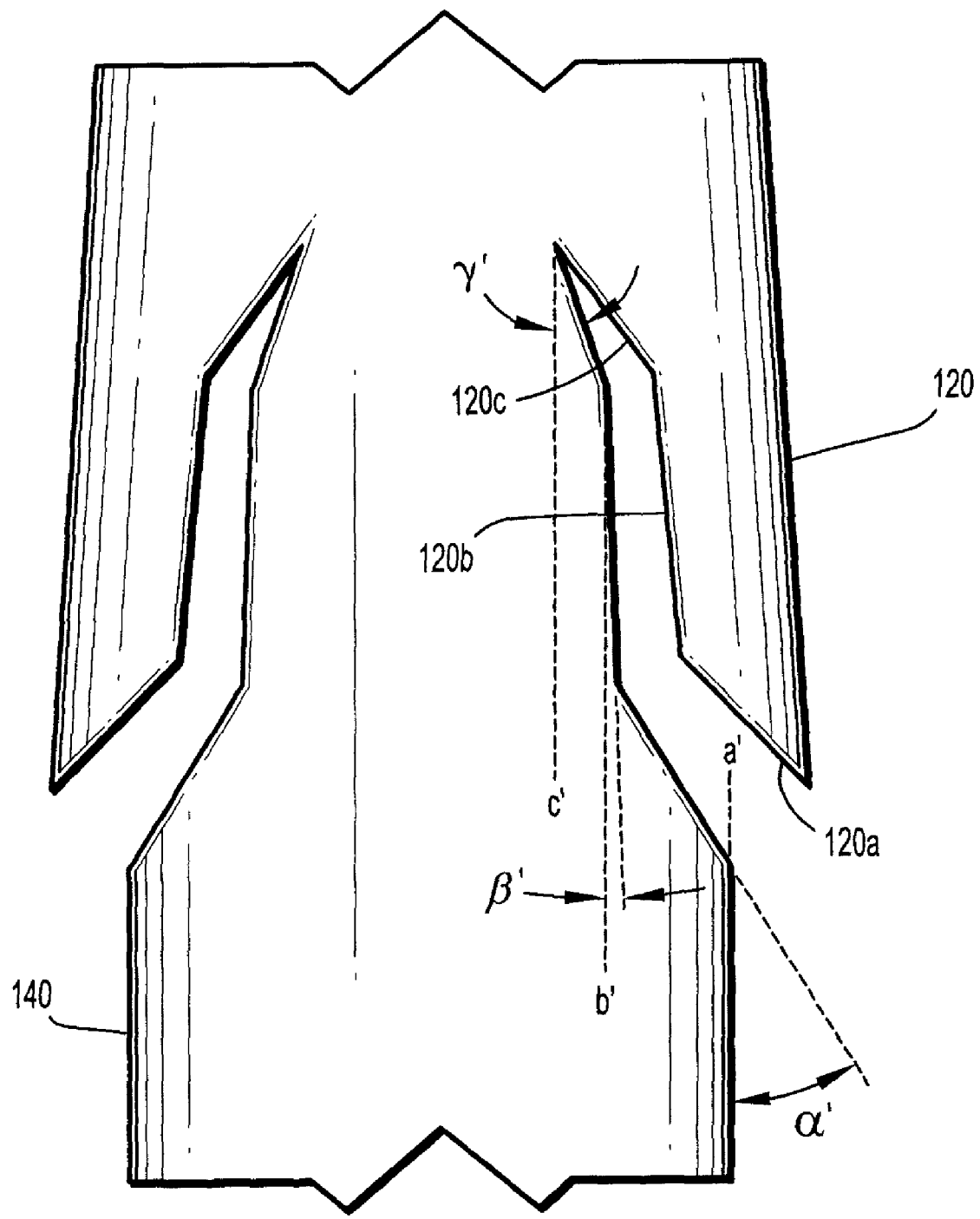
FIG. 4B is a plan view of an alternative embodiment of a segment of a barbed suture having compound barbs formed in accordance with the present disclosure.

Referring to FIG. 4B, each of the first, second and third portions 12a-c' may be cut at first, second and third angles $\alpha'$, $\beta'$, and $\gamma'$ relative to the longitudinal axes "a'", "b'", and "c'", respectively, of elongated body 140, such that angle $\alpha'$ is greater than angle $\beta'$ and angle $\gamma'$ is less than angle $\beta'$. Compound barb 120 may include a first portion 120a which is formed by cutting into elongated body 140 at a first angle $\alpha'$ of from about 0 degrees to about 90 degrees relative to longitudinal axis "a'", in other embodiments, the first angle $\alpha'$ ranges from about 30 degrees to about 50 degrees relative to longitudinal axis "a'", a second portion 120b which is formed by cutting into elongated body 140 at a second angle $\beta'$ of from about 0 degrees to about 90 degrees relative to longitudinal axis "b'", in other embodiments, a second angle $\beta'$ ranges from about 30 degrees to about 60 degrees relative to longitudinal axis "b'", and a third portion 12c which is formed by cutting into elongated body 140 at a third angle $\gamma'$ of from about 0 degrees to about 90 degrees relative to longitudinal axis "c'", in other embodiments, a third angle $\gamma'$ ranges from about 25 degrees to about 50 degrees relative to longitudinal axis "c'".

Figure 10:
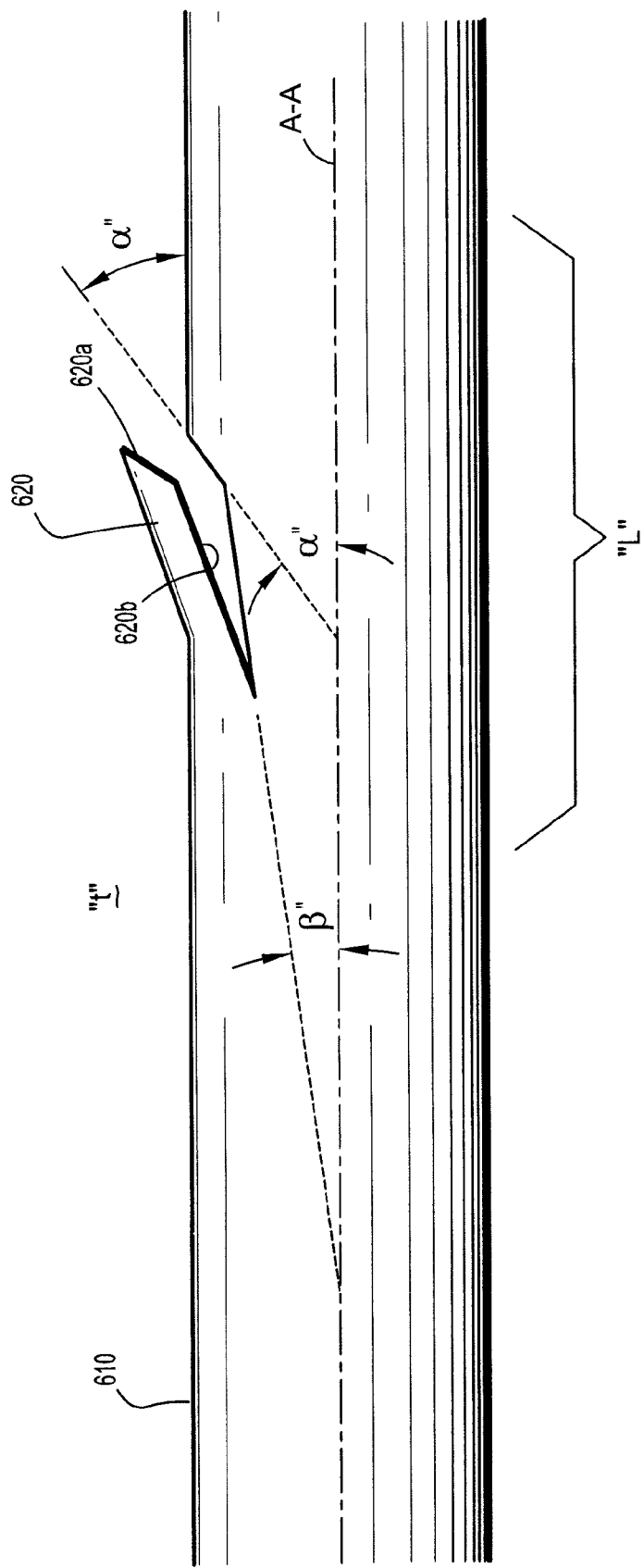
FIG. 10 is a plan view of an alternate embodiment of a segment of a barbed device having compound barbs formed in accordance with the present disclosure.

An alternate embodiment of a compound barb suture is shown in FIG. 10. The compound barb 620 includes two portions 620a, 620b which are disposed at two angles, $\alpha''$ and $\beta''$ relative to a longitudinal axis of the medical device. More specifically, the compound barb 620 includes a first portion 620a formed from the elongate body 610 at a first angle $\alpha''$, which is from about 0 degrees to about 90 degrees, in embodiments, from about 30 degrees to about 40 degrees, and in further embodiments, from about 31 degrees to about 38 degrees, relative to a longitudinal axis A-A of the elongate body 610. The second portion 620b is formed from the elongate body 610 at a second angle $\beta''$ which is from about 0 degrees to about 90 degrees, in embodiments, from about 1 degrees to about 10 degrees and in further embodiments, from about 1 degree to about 8 degrees relative to the longitudinal axis A-A of the elongate body 610.

Figure 11:
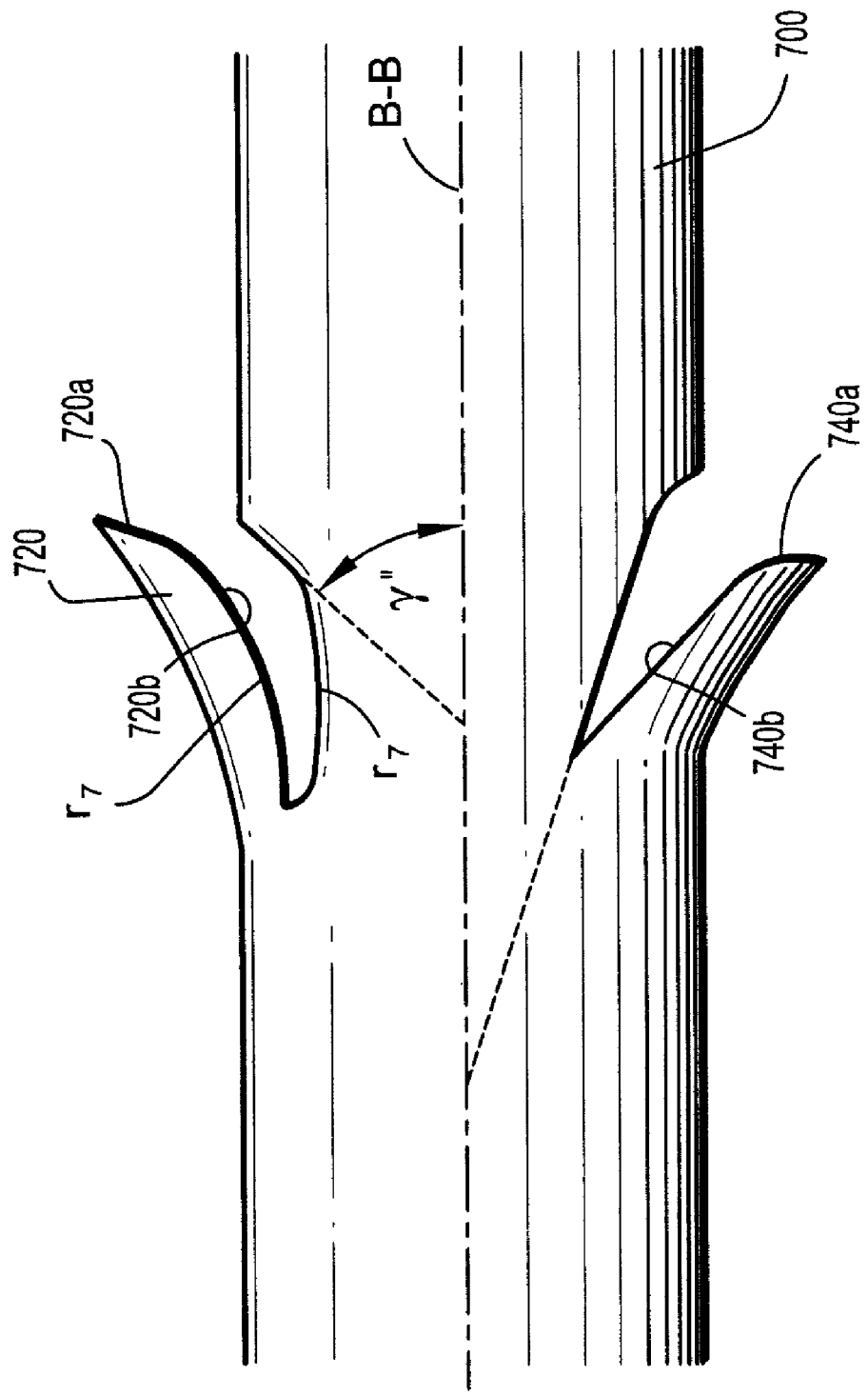
FIG. 11 is a plan view of another embodiment of a segment of a barbed device having compound barbs formed in accordance with the present disclosure.

Another embodiment of a compound barb device is shown in FIG. 11. An elongate body 700 is shown including a compound barb 720 having a first linear portion 720a, shown at an angle $\gamma''$, relative to a longitudinal axis B-B of the elongate body 700. Extending from the first portion 720a is an arcuate second portion 720b at a radius $r_7$. The elongate body 700 also includes a compound barb wherein a first portion 740a is arcuate and a second portion 740b is linear.

Figure 5:
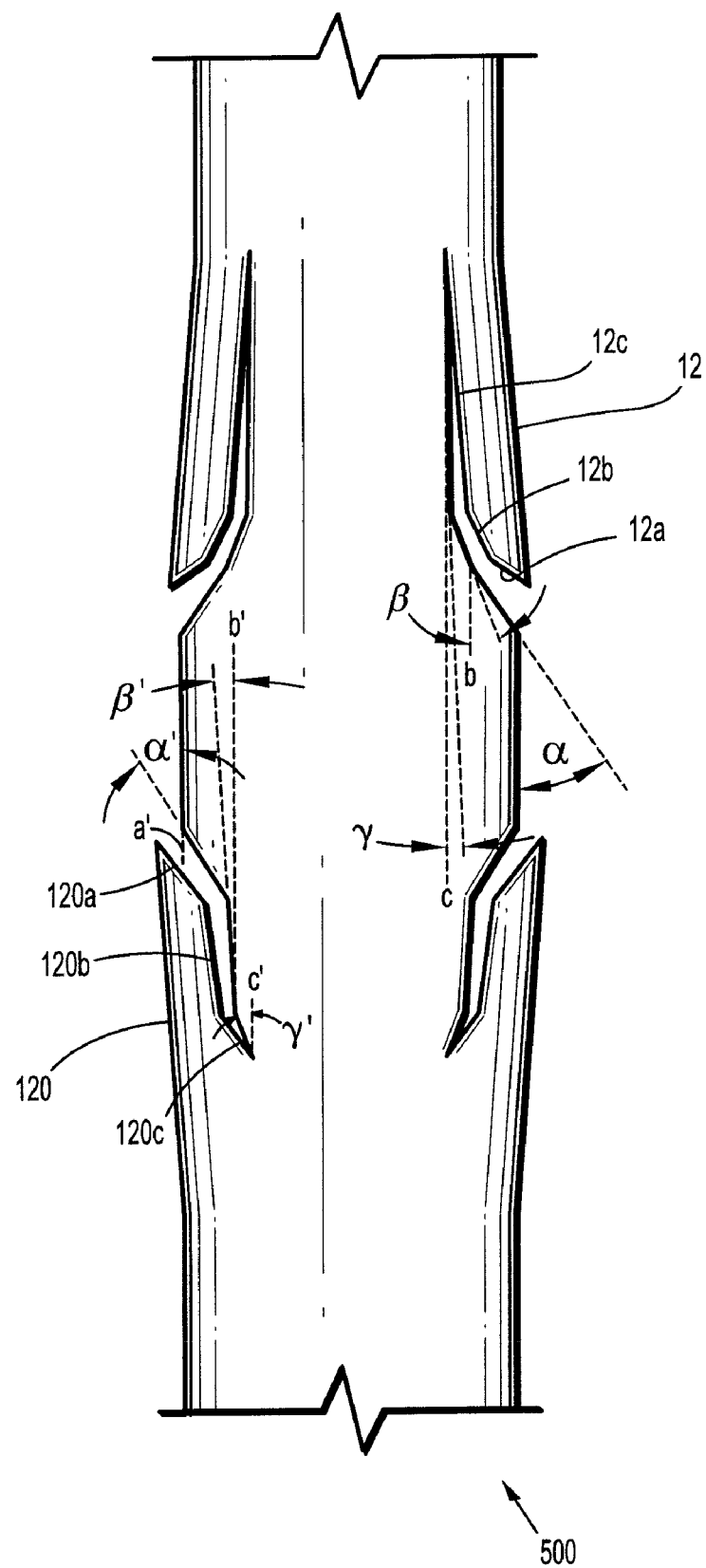
FIG. 5 is a plan view of a segment of a bidirectional barbed suture having compound barbs formed in accordance with the present disclosure.

FIG. 5 illustrates compound barb 12 having three portions 12a-c, as illustrated in FIGS. 4A and 5, and compound barb 120 having three portions 120a-c as illustrated in FIGS. 4B and 5, formed such that some of the barbs project toward one end and the remaining barbs project toward the other end so as to form a bidirectional medical device 500. In alternative embodiments, compound barbs are formed such that the barbs projecting toward one end, for example, towards the proximal end, have the same orientation and angles as the barbs projecting towards the other end, for example, towards the distal end.

Figure 6:
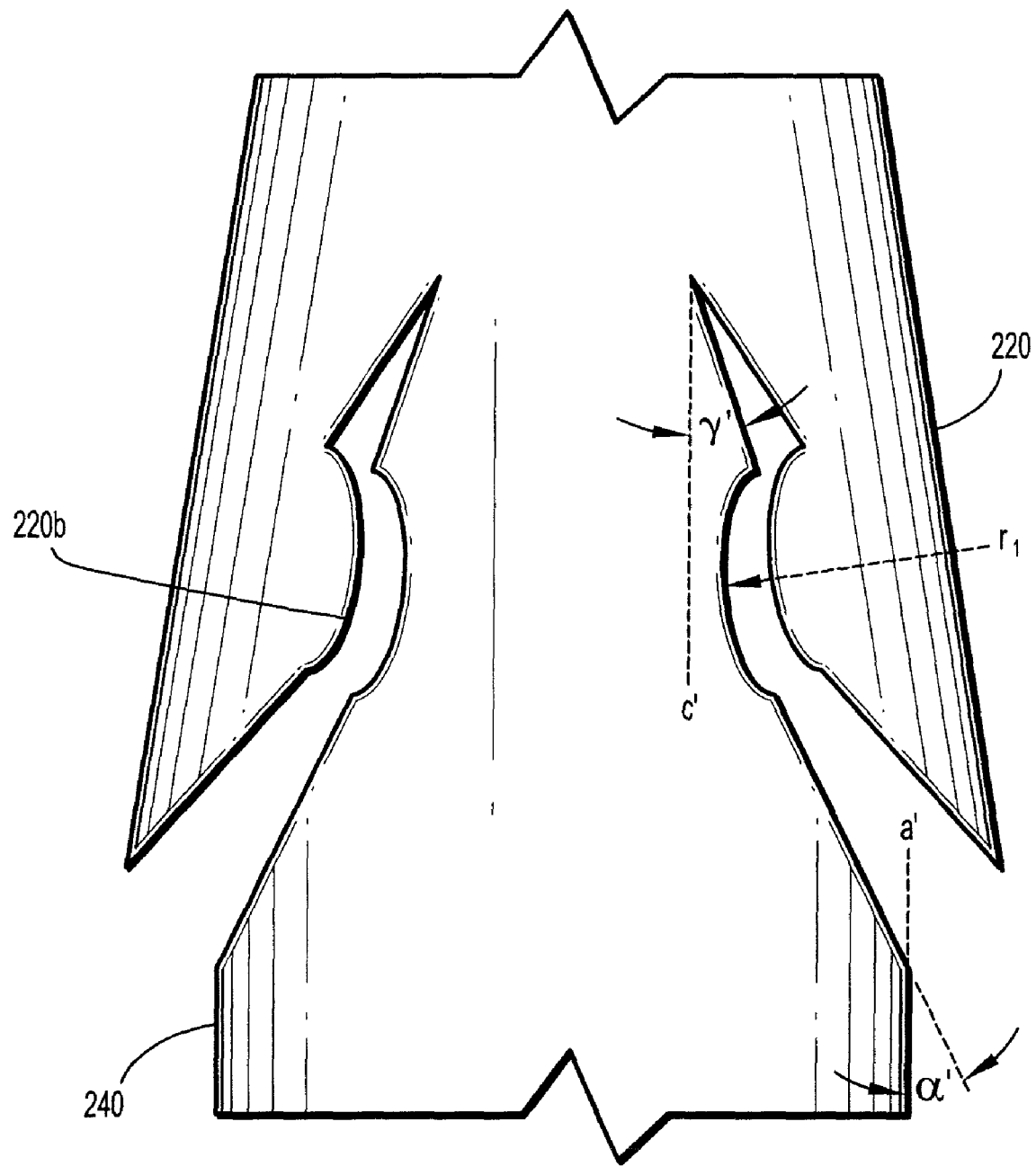
FIG. 6 is a plan view of an alternative embodiment of a barbed suture having compound barbs formed in accordance with the present disclosure.

In some embodiments, the compound barb may include at least one portion which is substantially non-linear. In embodiments, the barbs may include at least one point of inflection which may define a concave portion, a convex portion, an arcuate portion and combinations thereof. For example, at least one of the portions may be cut at a radius relative to the longitudinal axis of elongated body 240. As shown in FIG. 6, compound barb 220 may include an arcuate second portion 220b. The arcuate portion 220b may be cut at a radius $r_1$ relative to the longitudinal axis of elongated body 240.

Figure 7:
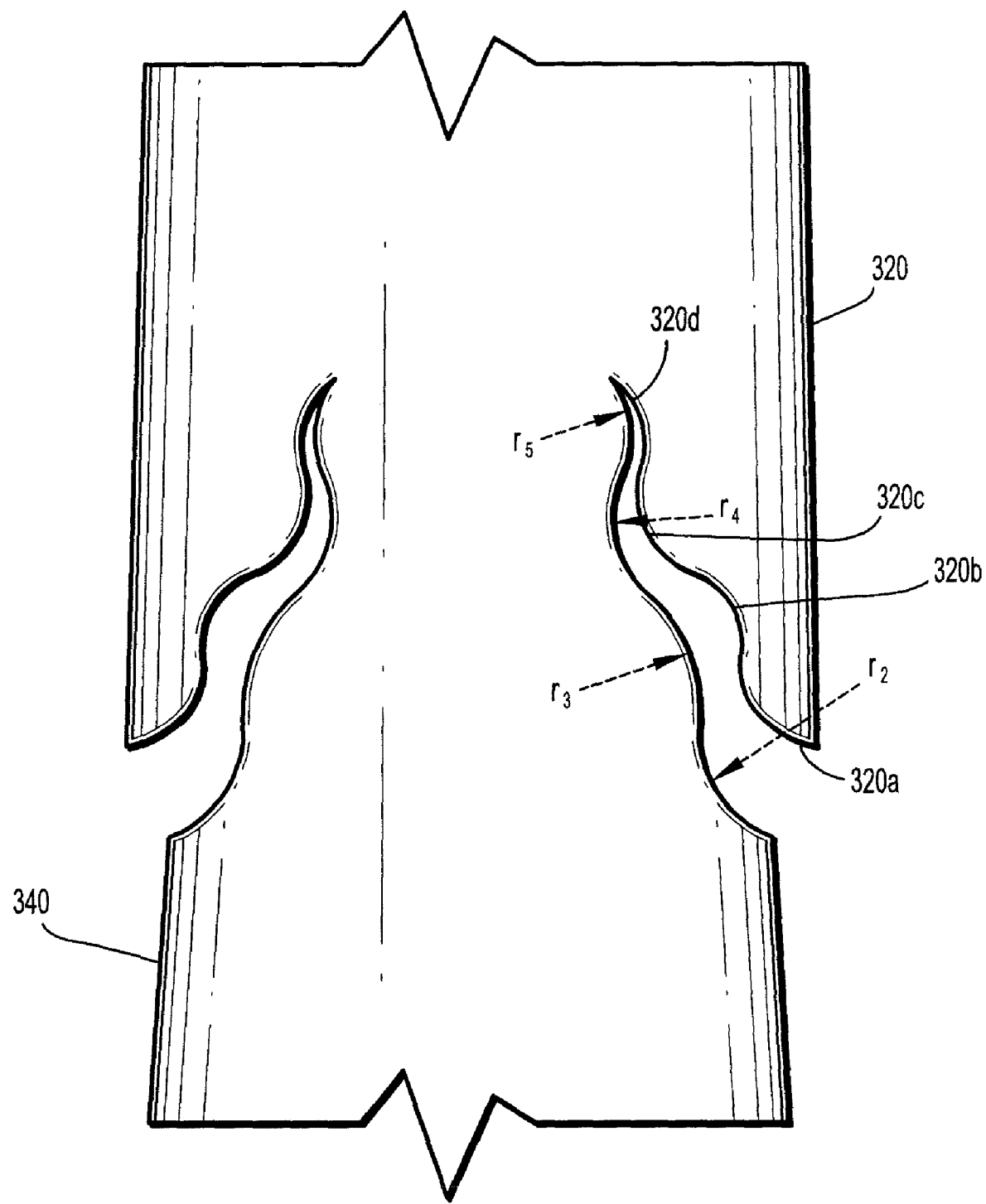
FIG. 7 is a plan view of an alternative embodiment of a barbed suture having compound barbs formed in accordance with the present disclosure.

In alternative embodiments, an optional fourth portion may be cut at a fourth radius. In some embodiments, each of the first, second, third and optional fourth portions 320a-d may be cut at first, second, third and fourth radii relative to the longitudinal axis of elongated body 340. As illustrated in FIG. 7, compound barb 320 may include an arcuate first portion 320a which extends away from elongated body 340 at a first radius $r_2$, an arcuate second portion 320b which extends from first portion 320a at a second radius $r_3$, an arcuate third portion 320c which extends from second portion 320b at a third radius $r_4$, an arcuate fourth portion 320d which extends from third portion 320c at a fourth radius $r_5$.

In other embodiments, a compound barb medical device may include an elongated body having a barb and first, second, and third portions being cut at first, second, and third angles respective to a longitudinal axis of the elongated body to form the barb.

The medical device in accordance with the present disclosure may be formed of the type selected from the group consisting of monofilament sutures, braided sutures, multifilament sutures, surgical fibers, anchors, slit sheets, ribbons, tape, mesh, stent, scaffolds, pledgets, vascular graft and ribbons. In an exemplary embodiment, the medical device is a suture.

The exemplary medical devices illustrated throughout the figures are shown to be elliptical in cross-sectional geometry. However, the cross-sectional geometry of the medical device may be of any suitable shape, for example, round, square, star shaped, octagonal, rectangular, polygonal and flat.

Figure 8:
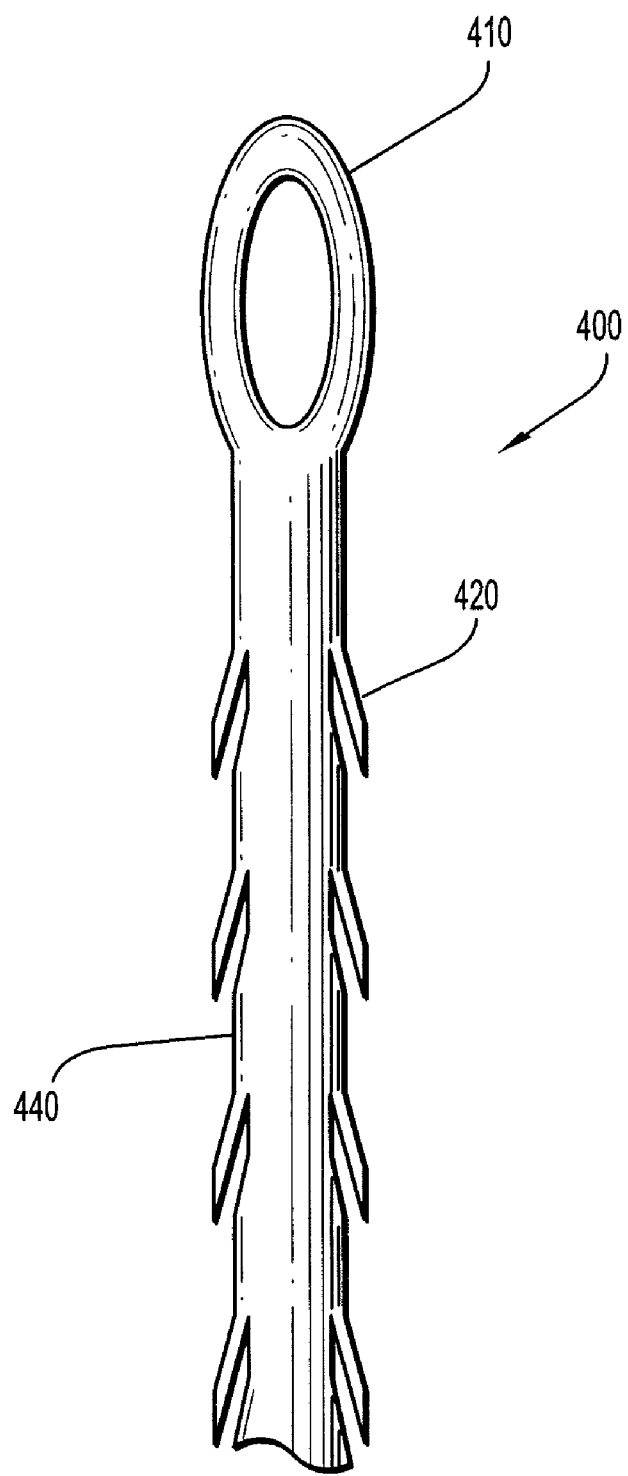
FIG. 8 is a plan view of a segment of a barbed suture having compound barbs and a loop formed at one end in accordance with the present disclosure.

In some embodiments, a loop is formed at the proximal end of the compound barb medical device which is configured to enhance retention of the device in body tissue at a desired position. As illustrated in FIG. 8, loop 410 is formed at the proximal end of the compound barb medical device 400. Loop 410 may be fixed at a predetermined location along the length of the elongated body 440 of the compound barb medical device 400. Loop 410 may be configured and dimensioned to be adjustable along the length of elongated body 440 (not shown).

In general, a method for forming a compound barb on a medical device includes the steps of providing a medical device having a longitudinal axis and forming a compound barb along the medical device wherein the compound barb defines an inner surface which includes at least a first portion disposed at a first orientation relative to the longitudinal axis, a second portion disposed at a second orientation relative to the longitudinal axis, and a third portion disposed at a third orientation relative to the longitudinal axis. In embodiments, at least one of the first, second, and third portions is substantially linear. In alternative embodiments, at least one of the first, second, and third portions is substantially non-linear or arcuate.

In embodiments, a method of forming a compound barb on a medical device includes forming a first cut in the medical device, the first cut having a first ratio of cut depth to diameter of the medical device; forming a second cut in the medical device, the second cut having a second ratio of cut depth to diameter of the medical device; and forming a third cut in the medical device, the third cut having a third ratio of cut depth to diameter of the medical device.

Figure 9:
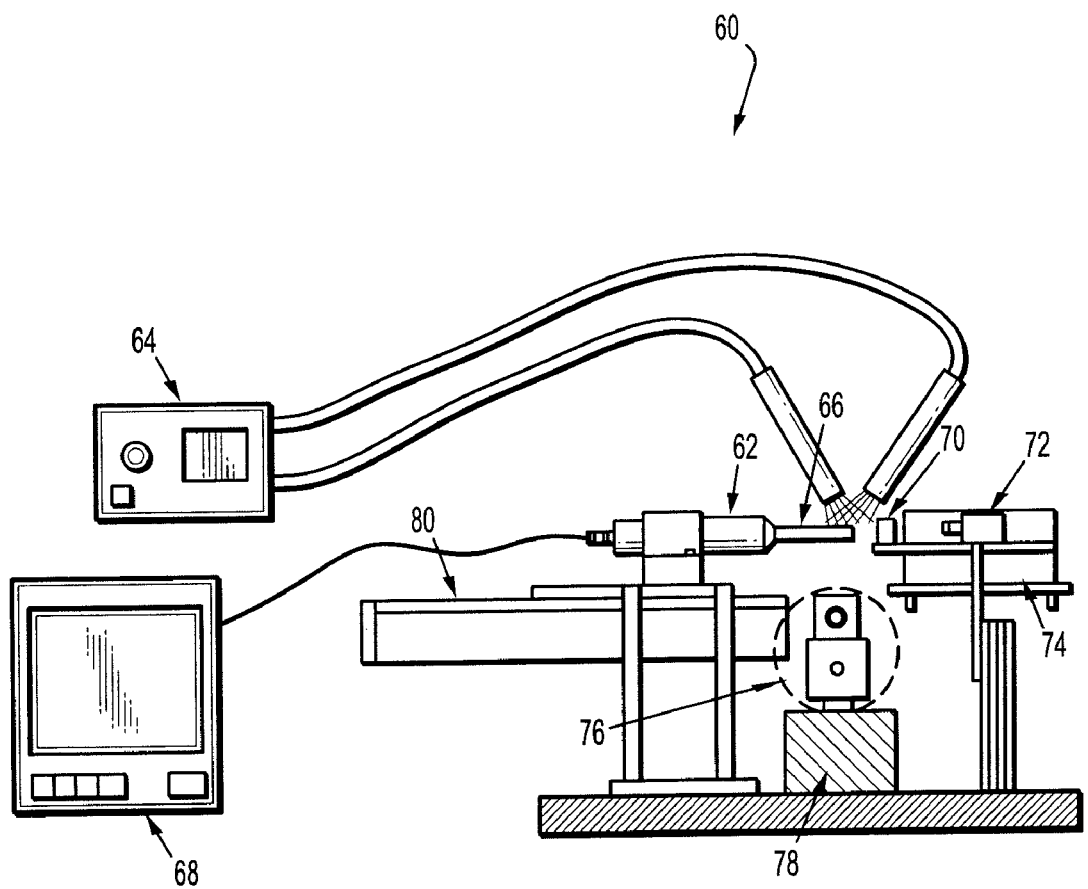
FIG. 9 is a schematic view of an embodiment of an apparatus and method of forming barbs on a medical device in accordance with the present disclosure.

FIG. 9 illustrates an embodiment of an apparatus and method of forming compound barbs in accordance with the present disclosure. The method is described, for example in U.S. Patent Application No. 60/994,173 filed Sep. 17, 2007 and titled "Method of Forming Barbs on a Suture", the entire disclosure of which is incorporated herein by reference. In the illustrative embodiment, the ultrasonic energy is generated by an apparatus 60 that includes a converter 62 which transmits ultrasonic energy to a horn 66 that is operatively coupled to converter 62. Converter 62 converts electrical energy to mechanical energy which causes displacement of the tool at an ultrasonic frequency powered by an ultrasonic generator or booster 68. Booster 68 may be manipulated to either increase or decrease the ultrasonic frequency which may be transmitted to the tool. The ultrasonic frequency may range from about 1 kHz to about 100 kHz. In other embodiments, the ultrasonic frequency may range from about 10 kHz to about 90 kHz. In still further embodiments, the ultrasonic frequency may range from about 15 kHz to about 50 kHz. The ultrasonic signal amplitude may range from about 1μ to about 125μ. In other embodiments, the signal amplitude may range from about 15μ to about 60μ.

The ratio of the cut depth and the angle of the barbs relative to the elongated body of the medical device are variable based on the signal amplitude of ultrasonic energy applied to the cutting element. For example, as the ultrasonic amplitude is increased, the ratio of the cut depth to the diameter and the angle of the barbs are decreased. As the ultrasonic amplitude is decreased, the ratio of the cut is increased.

Referring back to FIG. 4A, in some embodiments, the compound barbs 12 as formed have a first angle α of approximately 0 degrees to about 90 degrees, in embodiments, from 30 degrees to 50 degrees between compound barb 12 and elongated body 14 and a first ratio of cut depth which is approximately 1% to about 40%, and in certain embodiments, about 10% to about 30% of the diameter of the body.

Compound barb 12 as formed by the method of the present disclosure may have a second angle β of approximately 0 degrees to about 90 degrees, in embodiments, from 2 degrees to 25 degrees relative to the longitudinal axis with a second ratio of cut depth of approximately 5% to about 50%, and in certain embodiments, about 15% to about 45% of the diameter of elongated body 14. Compound barb 12 as formed by the method of the present disclosure may have a third angle γ of approximately 0 degrees to about 90 degrees, in embodiments, from about 25 degrees to about 50 degrees relative to the longitudinal axis with a third ratio of cut depth of approximately 15% to about 50%, and in some embodiments, from about 30% to about 50% the diameter of elongated body 14. In one embodiment, a plurality of barbs are formed at successive intervals along the longitudinal axis of the medical device.

With continued reference to FIG. 9, the apparatus 60 optionally includes a gripper such as anvil 70 for supporting a medical device. The gripper 70 supports the medical device at a fixed position. The horn 66 is configured and dimensioned to accept a cutting element such as a knife blade or a rotary blade (not shown) for forming the barbs on the medical device. The motorized slide 74 moves in an X, Y, and Z plane to allow the medical device to pass in front of the converter to form barbs thereon. Apparatus 60 also includes rotational motor 76 which rotates the medical device in a circular direction. Advance slide 78 moves the medical device after every cut a specified increment for the appropriate barb spacing. Apparatus 60 optionally includes camera 72 for recording the method of forming barbs and a light source 74 for optimizing the view of camera 72.

In embodiments, the medical device is moved to be contact with the cutting element, or in other embodiments, the medical device is moved against the cutting element, at a specified first angle relative to the longitudinal axis of the elongated body of the medical device and forming a first ratio of cut depth to the diameter of approximately 1% to about 40%, in other embodiments more particularly a first ratio of cut depth to the diameter of approximately 10% to about 30%. While the cutting element is still in contact with the medical device, a second angle is cut having a ratio of cut depth to diameter of approximately 5% to about 50%, in other embodiments more particularly a ratio of cut depth to diameter of approximately 15% to about 45%. Optionally, in other embodiments, while the cutting element is still in contact with the medical device, a third angle is cut having a ratio of cut depth to diameter of approximately 15% to about 50%, in other embodiments more particularly a ratio of cut depth to diameter of approximately 30% to about 50%. The amount of time the blade is in contact with the medical device ranges, in embodiments, from about 1 millisecond to about 5 seconds. In other embodiments, the amount of time the blade is in contact with the medical device ranges from about 1 second to about 3 seconds. In still further embodiments, the amount of time the blade is in contact with the medical device is about 2 seconds.

In embodiments, the knife blade may be shaped substantially into a rectangle shape, a square shape, a circle shape, a flat shape, an octagonal shape, a triangle shape, a star shape, a spade shape, an arrow shape, a key shape and an elliptical shape. In some embodiments, the curvature of the knife blade is substantially concave or substantially convex.

In practice, the medical device passes in front of the converter 62 which includes the horn 66 and the anvil 70, then using ultrasonic energy at various frequencies and signal amplitudes cut the material to a geometry. In embodiments, the medical device passes in front of converter 62 via motorized slide 74 which is configured and dimensioned to hold gripper 70 and camera 72 thereon. In certain embodiments, the medical device passes in front of converter 62, via a mechanical feeding mechanism with the medical device held tightly around two spools on each side of the apparatus (not shown). In other embodiments, the medical device passes in front of converter 62 via human manipulation of the medical device.

Still referring to FIG. 9, the apparatus 60 includes a converter 62 coupled to a horn 66 which operatively moves along a straight line X-Y plane via ultrasonic vibrational energy. The horn 66 includes a blade which contacts a surface of the medical device at an angle so as to form at least one barb on the medical device. The blade is appropriately positioned to contact the medical device via knife positioning slide 80. After each barb is formed, the medical device is moved in a linear motion on a X-Y plane via motorized slide 74 a specified length to allow another barb to be formed thereon. In embodiments, the medical device is moved in a X-Z plane via motorized slide 74 a specified length to form a barb thereon. In further embodiments, the medical device is moved in a Y-Z plane via motorized slide 74 a specified length to form a barb thereon. In alternative embodiments, the medical device is moved in a circular manner via rotational motor 76 to form a barb at a specified position. In embodiments, the medical device is moved in both a rotational and x-z plane rotation.

In practice, the barbs 12 are formed as either the knife blade or rotary blade (not shown) contacts the outer surface of the medical device. The blade may be urged into contact with the surface of the medical device, for example, by a reciprocating actuator in a straight line X-Y plane. It is contemplated, however, that in alternative embodiments, the blade may be held fixed and the medical device may be urged toward the blade. The blade makes contact with the surface of the medical device at an angle relative thereto such that the combined action of the movement of the blade into contact with the medical device surface and the ultrasonic vibration of the knife forms the desired barb. Advance slide 78 then moves the medical device after every cut a specified increment for the desired spacing of the barbs.

Ultrasonic energy may transfer heat to the medical device as it is forming the barbs thereon. Depending on the amplitude, the ultrasonic frequency may cause melting of medical device if the blades are left to penetrate medical device throughout the full wave cycle. To prevent this from occurring, in some embodiments, the application of ultrasonic energy is discontinued at some point prior to withdrawal of the blades from contact of the medical device. In other embodiments, this method may be used to vary the angle and the depth of the cut as indicated above with respect to the increase or decrease of the amplitude.

In some embodiments, barbs may be formed by making acute angular cuts directly into the medical device body, with cut portions pushed outwardly and separated from the body of the medical device. The depth of the barbs thus formed in the medical device body may depend on the diameter of the material and the depth of the cut.

In some embodiments, a suitable device for cutting a plurality of axially spaced barbs on the exterior of a filament may use a gripper as a cutting bed, a cutting bed vise, a cutting template, and a converter and horn as the blade assembly to perform the cutting. In operation, the cutting device has the ability to produce a plurality of axially spaced barbs in the same or random configuration and at different angles in relation to each other.

In other embodiments, the barbs may be arranged on a first portion of a length of the medical device body to allow movement of a first end of the medical device through tissue in one direction, while barbs on a second portion of the length of the medical device body may be arranged to allow movement of the second end of the medical device in an opposite direction.

The barbs can be arranged in any suitable pattern, for example, helical, spiral, linear, or randomly spaced. The pattern may be symmetrical or asymmetrical. The number, configuration, spacing and surface area of the barbs can vary depending upon the tissue in which the medical device is used, as well as the composition and geometry of the material utilized to form the medical device. Additionally, the proportions of the barbs may remain relatively constant while the overall length of the barbs and the spacing of the barbs may be determined by the tissue being connected. For example, if the medical device is to be used to connect the edges of a wound in skin or tendon, the barbs may be made relatively short and more rigid to facilitate entry into this rather firm tissue. Alternatively, if the medical device is intended for use in fatty tissue, which is relatively soft, the barbs may be made longer and spaced further apart to increase the ability of the suture to grip the soft tissue.

The surface area of the barbs can also vary. For example, fuller-tipped barbs can be made of varying sizes designed for specific surgical applications. For joining fat and relatively soft tissues, larger barbs may be desired, whereas smaller barbs may be more suitable for collagen-dense tissues. In some embodiments, a combination of large and small barbs within the same structure may be beneficial, for example when a suture is used in tissue repair with differing layer structures. In particular embodiments, a single directional suture may have both large and small barbs; in other embodiments a bidirectional suture may have both large and small barbs.

Medical device 100 in accordance with the present disclosure may be formed of absorbable materials, non-absorbable materials, and combinations thereof. More particularly, the medical device may be formed of an absorbable material selected from the group consisting of polyesters, polyorthoesters, polymer drugs, polyhydroxybutyrates, dioxanones, lactones, proteins, cat gut, collagens, carbonates, homopolymers thereof, copolymers thereof, and combinations thereof. In other embodiments, suitable absorbable materials which may be utilized to form the medical device include natural collagenous materials or synthetic resins including those derived from alkylene carbonates such as trimethylene carbonate, tetramethylene carbonate, and the like, caprolactone, glycolic acid, lactic acid, glycolide, lactide, homopolymers thereof, copolymers thereof, and combinations thereof. In some embodiments, glycolide and lactide based polyesters, especially copolymers of glycolide and lactide, may be utilized to form the medical device of the present disclosure.

Barbed medical devices fabricated from an absorbable material in accordance with the present disclosure maintain their structural integrity after implantation (e.g., about 80% of original strength) for a period of time, depending on the various processing parameter and the particular copolymer used. Such characteristics include, for example, the components of the copolymer, including both the monomers utilized to form the copolymer and any additives thereto, as well as the processing conditions (e.g., rate of copolymerization reaction, temperature for reaction, pressure, etc.), and any further treatment of the resulting copolymers, i.e., coating, sterilization, etc.

The formation of barbs on a suture body may be utilized to alter the degradation time of a suture in accordance with the present disclosure as described in U.S. patent application Ser. No. 11/556,002 filed on Nov. 2, 2006 entitled "Long Term Bioabsorbable Barbed Sutures", the entire contents of which are incorporated by reference herein.

For non-absorbable barbed medical devices constructed in accordance with the present disclosure, suitable non-absorbable materials which may be utilized to form the medical device include polyolefins, such as polyethylene, polypropylene, copolymers of polyethylene and polypropylene, and blends of polyethylene and polypropylene; polyamides (such as nylon); polyamines, polyimines, polyesters such as polyethylene terephthalate; fluoropolymers such as polytetrafluoroethylene; polyether-esters such as polybutesters; polytetramethylene ether glycol; 1,4-butanediol; polyurethanes; and combinations thereof. In other embodiments, non-absorbable materials may include silk, cotton, linen, carbon fibers, and the like. The polypropylene can be isotactic polypropylene or a mixture of isotactic and syndiotactic or atactic polypropylene.

The filaments and fibers used for forming the medical device of the present disclosure may be formed using any technique within the purview of those skilled in the art, such as, for example, extrusion, molding and/or solvent casting.

In one preferred embodiment, compound barbs are formed on a monofilament suture. A barbed monofilament suture may be preferred in embodiments where higher strength and longer absorption and strength profiles are preferred. The compound barb monofilament sutures may be preferred, for example, in dermal application where there is an increased risk of infection.

In some embodiments, devices of the present disclosure may include a yarn made of more than one filament, which may contain multiple filaments of the same or different materials. Where the devices are made of multiple filaments, the device can be made using any known technique such as, for example, braiding, weaving or knitting. The filaments may also be combined to produce a non-woven suture. The filaments themselves may be drawn, oriented, crinkled, twisted, commingled or air entangled to form yarns as part of the suture forming process.

In other embodiments, compound barb medical devices may include other medical devices such as braided sutures, surgical fibers, anchors, slit sheets, ribbons, tapes, meshes, stents, scaffolds, pledgets, and vascular grafts.

Once the medical device is barbed, it can be sterilized by any means within the purview of those skilled in the art.

Medical devices in accordance with the present disclosure may be coated or impregnated with one or more synthetic or natural polymers e.g., bioactive agents which accelerate or beneficially modify the healing process when the suture is applied to a wound or surgical site. In certain embodiments, the coating may be formed from absorbable polymers selected from the group consisting of lactones, carbonates, polyorthoesters, hydroxyalkoanates, hydroxybutyrates, bioactive agents, polyanhydrides, silicone, vinyl polymers, high molecular weight waxes and oils, natural polymers, proteins, polysaccharides, suspendable particulates, dispersible particulates, microspheres, nanospheres, rods, homopolymers thereof, copolymers thereof, and combinations thereof.

Suitable bioactive agents include, for example, biocidal agents, antimicrobial agents, antibiotics, anti-proliferatives, medicants, growth factors, anti-clotting agents, clotting agents, analgesics, anesthetics, anti-inflammatory agents, wound repair agents and the like, chemotherapeutics, biologics, protein therapeutics, monoclonal or polyclonal antibodies, DNA, RNA, peptides, polysaccharides, lectins, lipids, probiotics, diagnostic agents, angiogenics, anti-angiogenic drugs, polymeric drugs, and combinations thereof.

Bioactive agents include substances which are beneficial to the animal and tend to promote the healing process. For example, a suture can be provided with a bioactive agent that will be deposited at the sutured site. The bioactive agent can be chosen for its antimicrobial properties, capability for promoting wound repair and/or tissue growth, or for specific indications such as thrombosis. In embodiments, combinations of such agents may be applied to the medical device of the present disclosure after formation of the barbs.

The term "antimicrobial agent" as used herein includes an agent which by itself or through assisting the immune system, helps the body destroy or resist microorganisms which may be pathogenic. An antimicrobial agent includes antibiotics, antiseptics, quorum sensing blockers, antifungals, anti-virals, surfactants, metal ions, antimicrobial proteins and peptides, antimicrobial polysaccharides, disinfectants and combinations thereof. Antimicrobial agents which are slowly released into the tissue can be applied in this manner to aid in combating clinical and sub-clinical infections in a surgical or trauma wound site. In embodiments, suitable antimicrobial agents may be soluble in one or more solvents.

In embodiments, the following anti-microbial agents may be used alone or in combination with other bioactive agents described herein: an anthracycline, doxorubicin, mitoxantrone, a fluoropyrimidine, 5-fluorouracil (5-FU), a folic acid antagonist, methotrexate, mitoxantrone, quorum sensing blocker, brominated or halogenated furanones, a podophylotoxin, etoposide, camptothecin, a hydroxyurea, a platinum complex, cisplatin, doxycycline, metronidazole, trimethoprim-sulfamethoxazole, rifamycins like rifampin, a fourth generation penicillin (e.g., a ureidopenicillin a carboxypenicillin, meziocillin, piperacillin, carbenicillin, and ticarcillin, and an analogue or derivative thereof), a first generation cephalosporin (e.g., cephazolin sodium, cephalexin, cefazolin, cephapirin, and cephalothin), a carboxypenicillin (e.g., ticarcillin), a second generation cephalosporin (e.g., cefuroxime, cefotetan, and cefoxitin), a third generation cephalosporin (e.g., naxcel, cefdinir, cefoperazone, ceftazidime, ceftriaxone, and cefotaxime), polyvinyl pyrrolidone (PVP), a fourth generation cephalosporin (e.g., cefepime), a monobactam (e.g., aztreonam), a carbapenem (e.g., imipenem, ertapenem and meropenem), an aminoglycoside (e.g., streptomycin, gentamicin, tobramycin, and amikacin), an MSL group member (e.g., a macrolide, a long acting macrolide, a lincosamide, a streptogramin, Erythromycin, Azithromycin, Clindamycin, Syneroid, clarithromycin, and kanamycin sulfate), tetracyclines like minocycline, fusidic acid, trimethoprim, metronidazole; a quinolone (e.g., ciprofloxacin, ofloxacin, gatifloxacin, moxifloxacin, levofloxacin, and trovafloxacin), a DNA synthesis inhibitor (e.g., metronidazole), a sulfonamide (e.g. sulfamethoxazole, trimethoprim, including cefixime, spectinomycin, tetracycline, nitrofurantoin, polymyxin B, and neomycin sulfate), beta-lactam inhibitors like sulbactam, chloramphenicol, glycopeptides like vancomycin, mupirocin, polyenes like amphotericin B, azoles like fluconazole, and other known antimicrobial agent known in the art.

Examples of chemotherapeutics which may be utilized include one or more of the following: doxorubicin (Dox), paclitaxel (PTX), or camptothecin (CPT), polyglutamate-PTX (CT-2103 or Xyotax), N-(2-hydroxypropyl)methacrylamide (HPMA) copolymer, anthracycline, mitoxantrone, letrozole, anastrozole, epidermal growth factor receptor inhibitors, tyrosine kinase inhibitors, modulators of apoptosis, anthracycline antibiotics such as daunorubicin and doxorubicin, alkylating agents such as cyclophosphamide and melphalan, antimetabolites such as methotrexate and 5-fluorouracil, poly(ethylene glycol) (PEG), poly(glutamic acid) (PGA), polysaccharides, monoclonal antibody and polymer-drug conjugates thereof, copolymers thereof and combinations thereof.

The clotting agents include one or more of the following: a fibrosing agent that promotes cell regeneration, a fibrosing agent that promotes angiogenesis, a fibrosing agent that promotes fibroblast migration, a fibrosing agent that promotes fibroblast proliferation, a fibrosing agent that promotes deposition of extracellular matrix, a fibrosing agent that promotes tissue remodeling, a fibrosing agent that is a diverticular wall irritant, silk (such as silkworm silk, spider silk, recombinant silk, raw silk, hydrolyzed silk, acid-treated silk, and acylated silk), talc, chitosan, bleomycin or an analogue or derivative thereof, connective tissue growth factor (CTGF), metallic beryllium or an oxide thereof, copper, saracin, silica, crystalline silicates, quartz dust, talcum powder, ethanol, a component of extracellular matrix, oxidized cellulose, polysaccharides, collagen, fibrin, fibrinogen, poly(ethylene terephthalate), poly(ethylene-co-vinylacetate), N-carboxybutylchitosan, an RGD protein, a polymer of vinyl chloride, cyanoacrylate, crosslinked poly(ethylene glycol)-methylated collagen, an inflammatory cytokine, TGFβ, PDGF, VEGF, TNFa, NGF, GM-CSF, IGF-a, IL-1, IL-8, IL-6, a growth hormone, a bone morphogenic protein, a cell proliferative agent, dexamethasone, isotretinoin, 17-β-estradiol, estradiol, diethylstibesterol, cyclosporine a, all-trans retinoic acid or an analogue or derivative thereof, wool (including animal wool, wood wool, and mineral wool), cotton, bFGF, polyurethane, polytetrafluoroethylene, activin, angiopoietin, insulin-like growth factor (IGF), hepatocyte growth factor (HGF), a colony-stimulating factor (CSF), erythropoietin, an interferon, endothelin-1, angiotensin II, bromocriptine, methylsergide, fibrosin, fibrin, an adhesive glycoprotein, proteoglycan, hyaluronan, secreted protein acidic and rich in cysteine (SPaRC), a thrombospondin, tenacin, a cell adhesion molecule, dextran based particles, an inhibitor of matrix metalloproteinase, magainin, tissue or kidney plasminogen activator, a tissue inhibitor of matrix metalloproteinase, carbon tetrachloride, thioacetamide, superoxide dismutase to scavenge tissue-damaging free radicals, tumor necrosis factor for cancer therapy, colony stimulating factor, interferon, interleukin-2 or other lymphokines to enhance the immune system, platelet rich plasma, thrombin, peptides such as self assembly peptide systems, amino acids such as radA based amino acids, hydrogels such as super absorbing hydrogel materials, combinations thereof, and so forth.

A wide variety of anti-angiogenic factors may be readily utilized within the context of the present disclosure. Representative examples include Anti-Invasive Factor; retinoic acid and derivatives thereof; paclitaxel a highly derivatized diterpenoid; Suramin; Tissue Inhibitor of Metalloproteinase-1; Tissue Inhibitor of Metalloproteinase-2; Plasminogen Activator Inhibitor-1; Plasminogen Activator Inhibitor-2; various forms of the lighter "d group" transition metals such as, for example, vanadium, molybdenum, tungsten, titanium, niobium, and tantalum species and complexes thereof; Platelet Factor 4; Protamine Sulphate (Clupeine); Sulphated Chitin Derivatives (prepared from queen crab shells); Sulphated Polysaccharide Peptidoglycan Complex (SP-PG) (the function of this compound may be enhanced by the presence of steroids such as estrogen, and tamoxifen citrate); Staurosporine; Modulators of Matrix Metabolism, including for example, proline analogs {[(L-azetidine-2-carboxylic acid (LACA), cishydroxyproline, d,L-3,4-dehydroproline, Thiaproline, α,α-dipyridyl, β-aminopropionitrile fumarate; MDL 27032 (4-propyl-5-(4-pyridinyl)-2(3H)-oxazolone; Methotrexate; Mitoxantrone; Heparin; Interferons; 2 Macroglobulin-serum; ChIMP-3; Chymostatin; β-Cyclodextrin Tetradecasulfate; Eponemycin; Camptothecin; Fumagillin Gold Sodium Thiomalate ("GST"); D-Penicillamine ("CDPT"); β-1-anticollagenase-serum; α2-antiplasmin; Bisantrene; Lobenzarit disodium (N-(2)-carboxyphenyl-4-chloroanthronilic acid disodium or "CCA"; Thalidomide; Angostatic steroid; AGM-1470; carboxynaminolmidazole; metalloproteinase inhibitors such as BB94, analogues and derivatives thereof, and combinations thereof.

A wide variety of polymeric drugs may be readily utilized within the context of the present disclosure. Representative examples include steroidal anti-inflammatory agents, non-steroidal anti-inflammatory agents, and combinations thereof. Examples of the non-steroidal anti-inflammatory agent which may be used with the present disclosure are aspirin, indomethacin, ibuprofen, phenylbutazone, diflusinal, and combinations thereof.

Examples of the steroidal anti-inflammatory agent which may be used are glucocorticoids such as cortisone and hydrocortisone, betamethasone, dexamethasone, fluprednisolone, prednisone, methylprednisolone, prednisolone, triamcinolone, paramethasone, and combinations thereof.

Although the above bioactive agents have been provided for the purposes of illustration, it should be understood that the present disclosure is not so limited. In particular, although certain bioactive agents are specifically referred to above, the present disclosure should be understood to include analogues, derivatives and conjugates of such agents.

Medical devices in accordance with this disclosure can also include, for example, biologically acceptable plasticizers, antioxidants and colorants, which can be impregnated into the filament(s) utilized to form a suture of the present disclosure or included in a coating thereon.

Bioactive agents may be applied onto a barbed medical device of the present disclosure utilizing any method within the purview of one skilled in the art including, for example, dipping, spraying, vapor deposition, brushing, mixing, compounding and the like. In embodiments, a bioactive agent may be deposited within the barb angles, that is, the angle formed between the barb and the medical device surface in accordance with the present disclosure as described in U.S. patent application Ser. No. 11/899,852 filed on Sep. 6, 2007 entitled "Bioactive Substance in a Barbed Suture", the entire contents of which are incorporated by reference herein.

Medical devices of the present disclosure may contain additives such as dyes, pigments, and colorants in order to increase the visibility of the device in the surgical field. Any suitable agent such as those agents within the purview of those skilled in the art can be used in accordance with the present disclosure.

The filaments and sutures of the present disclosure may additionally include a needle at one end. In order to facilitate needle attachment to a suture of the present disclosure, conventional tipping agents can be applied to the braid. Two tipped ends of the suture may be desirable for attaching a needle to each end of the suture to provide a so-called double armed suture. The needle attachment can be made by any conventional method such as crimping, swaging, and the like.

In some cases, a tubular insertion device (not shown) may be utilized to introduce a barbed medical device in accordance with the present disclosure into tissue. Such a tubular insertion device may have a tubular body in which the barbed medical device of the present disclosure is disposed, as well as a distal end and a proximal end. In use, in some embodiments, the pointed end of a barbed suture of the present disclosure may be pushed with the distal end of the tubular insertion device through skin, tissue, and the like at an insertion point. The pointed end of the suture and the distal end of the tubular insertion device are pushed through the tissue until reaching an endpoint. The proximal end of the tubular insertion device is then gripped and pulled to remove the insertion device, leaving the barbed suture in place.

Barbed sutures and placement methods suitable for use according to the present disclosure are well known in the art. For example, in embodiments, medical devices of the present disclosure may be utilized to provide lift to tissue, which may be desirable in certain cosmetic applications. In some embodiments, a procedure for closing tissue utilizing barbed sutures includes inserting a first end of a monofilament suture, optionally attached to a needle, at an insertion point through the body tissue. The first end of the suture may be pushed through body tissue until the first end extends out of the body tissue at an exit point. The first end of the monofilament suture may then be gripped and pulled to draw the first portion of the suture through the body tissue so that an outer surface of the elongate body (of the first portion) of the suture remains in direct contact with the body tissue between the point of insertion and exit point of the first end. As shown, for example in FIG. 10, the outer surface 630 of the elongate body 610 is in direct contact with tissue "T." The outer surface 630 may be in direct contact with tissue "T" for any length "L" of the elongate body and is not limited to the contact length "L" as shown in FIG. 10. The body tissue may then be manually grouped and advanced along at least one portion of the monofilament suture to provide the desired amount of lift.

The medical devices of the present disclosure may be utilized in any cosmetic, endoscopic or laparoscopic methods. In addition, sutures of the present disclosure may be utilized to attach one tissue to another including, but not limited to, attaching tissue to a ligament. Specific applications of cosmetic surgeries include, for example, facelifts, browlifts, thigh lifts, and breast lifts.

While the above description contains many specifics, these specifics should not be construed as limitations on the scope of the disclosure, but merely as exemplifications of embodiments thereof. Those skilled in the art will envision many other possibilities within the scope and spirit of the disclosure as defined by the claims appended hereto.

What is claimed is:

1. A compound barb medical device comprising:
   an elongated body;
   at least one barb extending from the elongated body and the barb defining an inner surface opposite an outer surface of the elongated body, the inner surface including:
      a first portion disposed at a first orientation relative to a longitudinal axis of the elongated body,
      a second portion disposed at a second orientation relative to the longitudinal axis, and
      a third portion disposed at a third orientation relative to the longitudinal axis,
   wherein the outer surface of the elongated body has a complementary shape with the inner surface of the barb.

2. The compound barb medical device according to claim 1, wherein at least one of the first, second, and third portions is substantially linear.

3. The compound barb medical device according to claim 2, wherein the first, second, and third portions are at first, second, and third angles relative to respective longitudinal axes of the elongated body.

4. The compound barb medical device according to claim 3, wherein the first angle is about 0 degrees to about 90 degrees.

5. The compound barb medical device according to claim 3, wherein the second angle is about 0 degrees to about 90 degrees.

6. The compound barb medical device according to claim 3, wherein the third angle is about 0 degrees to about 90 degrees.

7. The compound barb medical device according to claim 1, wherein at least one of the first, second, and third portions is substantially non-linear.

8. The compound barb medical device according to claim 1, wherein the medical device is formed of the type selected from the group consisting of monofilament sutures, multifilament sutures, surgical fibers, anchors, slit sheets, ribbons, tapes, meshes, stents, scaffolds, pledgets, and vascular grafts.

9. The compound barb medical device according to claim 1, wherein the medical device is a suture.

* * * * *